US009457346B2

(12) United States Patent
Ouyang et al.

(10) Patent No.: US 9,457,346 B2
(45) Date of Patent: Oct. 4, 2016

(54) HIGHLY ACTIVE, SELECTIVE, ACCESSIBLE, AND ROBUST ZEOLITIC TI-EPOXIDATION CATALYST

(71) Applicants: The Regents of the University of California, Oakland, CA (US); Chevron U.S.A. Inc., San Ramon, CA (US)

(72) Inventors: Xiaoying Ouyang, El Cerrito, CA (US); Stacey Ian Zones, San Francisco, CA (US); Alexander S. Katz, Richmond, CA (US)

(73) Assignees: The Regents of the University of California, Oakland, CA (US); Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/847,700

(22) Filed: Sep. 8, 2015

(65) Prior Publication Data
US 2016/0067694 A1   Mar. 10, 2016

Related U.S. Application Data

(60) Provisional application No. 62/047,447, filed on Sep. 8, 2014.

(51) Int. Cl.
*C07D 301/02* (2006.01)
*B01J 29/89* (2006.01)
*C07D 301/19* (2006.01)

(52) U.S. Cl.
CPC ............. *B01J 29/89* (2013.01); *C07D 301/19* (2013.01)

(58) Field of Classification Search
CPC ............................ B01J 29/89; C07D 301/19

USPC ......................................................... 549/518
See application file for complete search history.

(56) References Cited

U.S. PATENT DOCUMENTS

| 7,084,305 B2 | 8/2006 | Zones et al. |
| 2006/0142601 A1* | 6/2006 | Zones ...................... B01J 29/70 549/533 |

OTHER PUBLICATIONS

Ogino et al, Heteroatom-Tolerant Delamination of Layered Zeoltie Precursor Materials,Chem. Mater., 2013, 25, p. 1502-1509.*
Corma et al,Oxidation of olefins with hydrogen peroxide and tert-butyl hydroperoxide on Ti-Beta catalyst, Journal of Catalysis , 1995, 152, p. 18-24.*
International Search Report from corresponding application PCT/US15/048918 mailed Jun. 23, 2016.
Nur, H., et al., "Phase-boundary catalysis of alkene epoxidation with aqueous hydrogen peroxide using amphiphilic zeolite particles loaded with titanium oxide" Journal of Catalysis, 2001, vol. 204, No. 2, pp. 402-408.
Jarupatrakorn, J., et al., "Silica-supported, single-site titanium catalysts for olefin epoxidation. A molecular precursor strategy for control of catalyst structure", Journal of the American Chemical Society, 2002, vol. 124, No. 28, pp. 8380-8388.
van der Waal, J. C., et al., "Zeolite titanium beta: A versatile epoxidation catalyst. Solvent effects", Journal of Molecular Catalysis A: Chemical, 1997, vol. 124, No. 2, pp. 137-146.
Ogino, I. et al., "Heteroatom-Tolerant Delamination of Layered Zeolite Precursor Materials", Chemistry of Materials, 2013, vol. 25, No. 9, pp. 1502-1509.

* cited by examiner

*Primary Examiner* — T. Victor Oh
(74) *Attorney, Agent, or Firm* — E. Joseph Gess; Melissa M. Hayworth

(57) ABSTRACT

Provided is a process of conducting olefin epoxidation which comprises contacting an olefin and an oxidant in the presence of Ti-UCB-4 to thereby prepare an epoxide. The Ti-UCB-4 catalyst is prepared by delaminating a B-SSZ-70 precursor and substituting Ti atoms for the boron atoms on the surface of the zeolite material lattice framework.

18 Claims, 5 Drawing Sheets

HIGHLY ACTIVE, SELECTIVE, ACCESSIBLE, AND ROBUST ZEOLITIC TI-EPOXIDATION CATALYST

RELATED APPLICATIONS

This application claims priority to U.S. Provisional No. 62/047,447, filed Sep. 8, 2014, the contents of which are incorporated herein by reference in their entirety.

BACKGROUND OF THE INVENTION

1. Field of the Invention

The current invention describes the use of framework-substituted zeolitic catalysts that are synthesized by substituting framework heteroatoms for B on the external surface of a zeolitic material. In a particular embodiment of this invention, the heteroatom is Ti and the Lewis-acid catalyst is a solid epoxidation catalyst that uses organic hydroperoxide as oxidant. Also described are the surprisingly advantageous properties of the resulting epoxidation catalyst in terms of its accessibility, activity, selectivity, and general robustness, all of which crucially depend on the nature of the zeolitic framework.

2. Description of the Related Art

Zeolites demonstrate extraordinary catalytic utility due to their well-defined catalytic active sites consisting of heteroatoms substituted within the zeolitic framework as well as shape selectivities. However, zeolites have been limited to microporous frameworks in the past, which has limited reactant substrates to small molecules. Incorporating greater accessibility into zeolite catalysts would be invaluable to expanding the scope of their catalysis to include larger and sterically more bulky substrate and product molecules.

MWW layered zeolite precursors, when substituted with metal heteroatoms, have shown catalytic activity using sterically bulky reactants, such as Ti-catalyzed epoxidation of cyclooctene using tertbutylhydroperoxide as oxidant; Al-catalyzed cracking of 1,3,5-triisopropylbenzene, and Sn-catalyzed Baeyer-Villiger oxidation of 2-adamantanone (Wang, L.; Wang, Y.; Liu, Y.; Chen, L.; Cheng, S.; Gao, G.; He, M.; Wu, P. *Microporous and Mesoporous Materials* 2008, 113, 435; Wang, Y.; Liu, Y.; Wang, L.; Wu, H.; Li, X.; He, M.; Wu, P. *Journal of Physical Chemistry C* 2009, 113, 18753; and Liu, G.; Jiang, J.-G.; Yang, B.; Fang, X.; Xu, H.; Peng, H.; Xu, L.; Liu, Y.; Wu, P. *Microporous and Mesoporous Materials* 2013, 165, 210.) Another promising approach for synthesis of accessible zeolites is the transformation of three-dimensional UTL germanosilicate into a two-dimensional lamellar zeolite by Cejka et al., who demonstrated that layers are separated during hydrolysis of the double-four ring (D4R) bridging units by hydrolysis (Roth, W. J.; Shvets, 0. V.; Shamzhy, M.; Chlubna, P.; Kubu, M.; Nachtigall, P.; Cejka, J. *Journal of the American Chemical Society* 2011, 133, 6130; and Chlubna, P.; Roth, W. J.; Greer, H. F.; Zhou, W.; Shvets, 0.; Zukal, A.; Cejka, J.; Morris, R. E. *Chemistry of Materials* 2013, 25, 542.) This latter approach, while elegant, requires precursors to consist of D4R units in the space between layers, such that D4R removal via hydrolysis results in two-dimensional zeolite layers, and has only been synthetically demonstrated on zeolite UTL.

Borosilicate zeolites have historically been generally considered to be less useful for acid-catalyzed reactions because their intrinsically weak acidity can effectively catalyze reactions that require mild acidity (Millini, R.; Perego, G.; Bellussi, G. *Topics in Catalysis* 1999, 9, 13; Chen, C. Y.; Zones, S. I.; Hwang, S. J.; Bull, L. M. In *Recent Advances in the Science and Technology of Zeolites and Related Materials, Pts a-C*; VanSteen, E., Claeys, M., Callanan, L. H., Eds. 2004; Vol. 154, p 1547; and Chen, C. Y., Zones, S. I. In 13*th International Zeolite Conference*; Galarneau, A., Di Renzo, F., Fujula, F., Vedrine, J., Eds.; Elsevier: Amsterdam, 2001, p paper 26.) However, borosilicate zeolites provide a unique route for synthesizing many types of isomorphous forms of zeolites at certain Si/M ratios (M=Al, Ga, Ti, etc.), which offer opportunities for synthesizing heteroatom-substituted metallosilicate zeolites, where the metal ions might otherwise be difficult to incorporate into the framework during direct synthesis (Chen, C. Y.; Zones, S. I. In 13*th International Zeolite Conference*; Galarneau, A., Di Renzo, F., Fujula, F., Vedrine, J., Eds.; Elsevier: Amsterdam, 2001, p paper 11.) In such a modification of one framework metal for another, the B atoms template certain T-positions in the zeolitic framework, and silanol nests can be created upon deboronation (Deruiter, R.; Kentgens, A. P. M.; Grootendorst, J.; Jansen, J. C.; Vanbekkum, H. *Zeolites* 1993, 13, 128; and Hwang, S. J.; Chen, C. Y.; Zones, S. I. *Journal of Physical Chemistry B* 2004, 108, 18535.)

Aluminum (Al) heteroatoms have been exchanged or substituted for boron (B) heteroatom in zeolites for many years. This exchange changes a weak acid zeolite into one that is more highly acid. Catalysis by acid sites can impact rates of chemical reaction, rates of mass transfer, selectivity to products and deactivation of the catalytic site or pore system. Better control of the acid sites would help to provide selective control of the overall catalysis.

Though substitution of aluminum for boron has previously been used, the result has been the extremes: the use of 10-MR zeolites where essentially no heteroatom exchange occurs (e.g., ZSM-11) or the use of large- or extra-large pore zeolites where essentially all B heteroatoms are exchanged (e.g., SSZ-33). See, for example, Chen, C. Y.; Zones, S. I., "Method for Heteroatom Lattice Substitution in Large and Extra-Large Pore Borosilicate Zeolites," U.S. Pat. No. 6,468,501 B1, Oct. 22, 2002; Chen, C. Y.; Zones, S. I., "Method to Improve Heteroatom Lattice Substitution in Large and Extra-Large Pore Borosilicate Zeolites," U.S. Pat. No. 6,468,501 B1, Sep. 14, 2004; Chen, C. Y.; Zones, S. I. *In Studies in Surface Science and Catalysis*"; Galarneau, A., Fajula, F., Di Renzo, F., Vedrine, J., Eds.; Elsevier: 2001; Vol. 135; Chen, C. Y.; Zones, S. I. *In Zeolites and Catalysis*; and Čejka, J., Corma, A., Zones, S. I., Eds. 2010, Vol. 1, p. 155. In these instances, acidic conditions are preferred to prevent dissolution of Si from the framework. In the aqueous $Al(NO_3)_3$ solution used, the hydrated aluminum cations used in the Al-exchange are too large to enter the 10-MR pores such as ZSM-11. See, for example, Chen, C. Y.; Zones, S. I. *In Studies in Surface Science and Catalysis*, Galarneau, A., Fajula, F., Di Renzo, F., Vedrine, J., Eds., Elsevier: 2001, Vol. 135; Chen, C. Y.; Zones, S. I. *In Zeolites and Catalysis*, Čejka, J., Corma, A., Zones, S. I., Eds. 2010, Vol. 1, p. 155. In the Al-exchange of B-SSZ-33, the Si/B values increase from 18 to more than 200, and Si/Al values from 12 to 24, indicating exchange of most B heteroatoms for Al. See, Chen, C. Y.; Zones, S. I. *In Studies in Surface Science and Catalysis*, Galarneau, A., Fajula, F., Di Renzo, F., Vedrine, J., Eds., Elsevier: 2001, Vol. 135. The result is that either all or none of the boron was exchanged. No selective control is possible.

Catalysis by MCM-22, an aluminosilicate containing Al heteroatoms throughout the lattice framework, and therefore in all three pore systems, is characterized as between a large- and a medium-pore zeolite because it consists of both 10-MR (medium) and 12-MR (large) pores. The role of the acid sites on the external surface hemicages has been determined to differ from those of the internal pore systems through experiments that poison or coke (i.e., formation of carbonaceous deposits in the pore system) the catalytic sites. See, Laforge, S.; Martin, D.; Paillaud, J. L.; Guisnet, M. *J. Catal.* 2003, 220, 92; Laforge, S.; Martin, D.; Guisnet, M. *Microporous Mesoporous Mater.* 2004, 67, 235; Laforge, S.; Martin, D.; Guisnet, M. *Appl. Catal. A: Gen.* 2004, 268, 33; Matias, P.; Lopes, J. M.; Laforge, S.; Magnoux, P.; Guisnet, M.; Ramôa Ribeiro, F. *Appl. Catal. A: Gen.* 2008, 351, 174; Matias, P.; Lopes, J. M.; Laforge, S.; Magnoux, P.; Russo, P. A.; Ribeiro Carrott, M. M. L.; Guisnet, M.; Ramôa Ribeiro, F. *J. Catal.* 2008, 259, 190.

To selectively be able to use acid sites on the external surface would greatly improve one's ability to control a catalysis, and would be of great value to the industry. Moreover, to be able to further enhance a particular reaction by selecting the correct framework of the catalyst would yield even greater benefits to the industry.

SUMMARY OF THE INVENTION

Provided is a process of conducting olefin expoxidation. The process comprises contacting an olefin and an oxidant in the presence of a catalyst to thereby prepare an epoxide. The catalyst is prepared by delaminating a B-SSZ-70 precursor and substituting Ti atoms for the boron atoms on the external surface of the zeolite material lattice framework. Ti-UCB-4 is one such catalyst. The olefin, in one embodiment, can have from 3-12 or more carbon atoms. Examples include propylene and octene. The oxidant in one embodiment is tert-butylhydroperoxide (TBHP).

Among other factors, it has been found that by using framework substituted zeolitic catalysts that are synthesized by substituting framework heteroatoms for boron on the external surface of a zeolite material, and in this case Ti atoms, surprising advantages are realized for catalysis of epoxidation reactions. These advantages relate to the accessibility, activity, selectivity and general robustness of the catalyst in the epoxidation reaction. All of the advantages have been found to depend on the nature of the zeolitic framework, which includes the Ti heteroatom on the external surface of the zeolite material.

DETAILED DESCRIPTION OF THE PREFERRED EMBODIMENTS

Figure 1A:
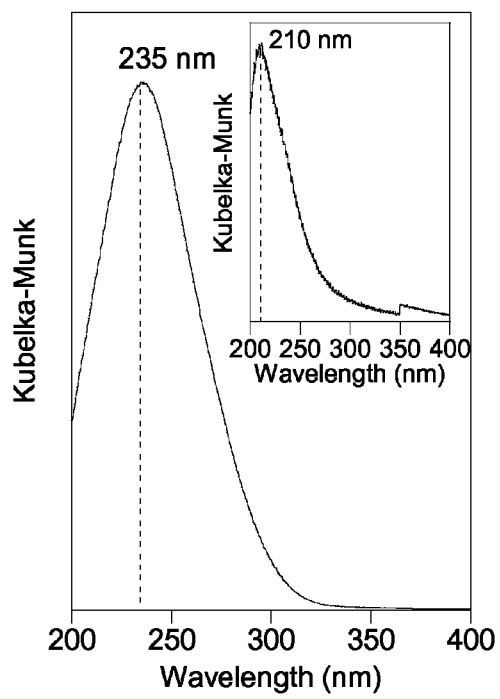
FIG. 1A shows DR-UV data characterizing Ti-DZ-1 and FIG. 1B shows DR-UV data characterizing Ti-UCB-4. The insets in FIGS. 1A and 1B' show the DR-UV data characterizing the samples after acid treatment.

Provided is a process of conducting an epoxidation reaction using a selected zeolite framework catalyst. The catalyst is prepared by a method employing a multistep framework substitution of B heteroatoms of a zeolite, with another heteroatom, in this case Ti, on the external-zeolite surface. This multistep procedure involves first deboronating the zeolite to expose a silanol nest in the framework position previously occupied by B, followed by reaction of the silanol nest with a heteroatom precursor molecule, so as to condense the precursor into the framework, which is substantially similar to the framework position previously occupied by B. In this way, the material comprising the silanol nest is an intermediate between the initial material and final heteroatom-containing catalytic material used in the present invention. This general procedure is described in U.S. patent application Ser. No. 14/185,115, "Novel Zeolitic Materials With Heteroatom Substitutions On External Surface Of Lattice Framework", filed Feb. 20, 2014, which application and its disclosure is expressly incorporated herein by reference in its entirety. In an alternate embodiment, substitution of Lewis-acid catalytic heteroatoms into framework positions on the external surface can be accomplished in a delaminated zeolitic material. Examples of such materials are provided in U.S. patent application Ser. No. 13/161,091, "Novel Oxide Material And Snythesis By Fluoride/Chloride Anion Promoted Exfoleation", filed Jun. 15, 2011, which application is expressly incorporated herein by reference in its entirety; and, U.S. patent application Ser. No. 14/291,489, "Delamination Of Borosilieate Layered Zeolite Precursors," filed May 30, 2014, which application is expressly incorporated by reference herein in its entirety. The advantage of delaminated materials is their generally greater external surface area (on a per gram basis) relative to the three-dimensional (undelaminated) zeolite counterparts. This leads to higher heteroatom loadings upon substitution and, ultimately, higher catalytic activity due to the higher accessible heteroatom-active-site number density, relative to what is available in the three-dimensional (undelaminated) zeolite counterpart.

In one particular embodiment of the present invention, the metal centers are represented by isolated grafted Ti(IV) atoms within a non-octahedral environment, such as tetrahedral or distorted tetrahedral, whereas the inorganic-oxide surface is the surface of silica, and more preferably silica with a high surface area. The conventional catalyst in contrast consists of grafted Ti(IV) sites on the surface of amorphous silica. Such a catalyst is known to be highly selective and active catalysts for the epoxidation of olefins using organic hydroperoxide as oxidant, and forms the basis for commercial processes for the production of propylene oxide.

In a preferred embodiment of the present invention, the Ti site is made more catalytically active, selective, and robust by virtue of it being a Ti heteroatom that is located within the zeolitic framework. A crucial feature of zeolitic environment is to enforce a particular geometry surrounding the Ti atom in terms of bond angles and distances between framework oxygens. This geometry is conducive to rendering the Ti site more catalytically active, selective, and robust, in a manner that depends crucially on the identity, connectivity, and structure of the zeolite framework.

In a most preferred embodiment of the present invention, the resulting catalyst is active for the olefin epoxidation of both terminal and internal alkenes using hydrogen peroxide as the oxidant, and comprises a material in which Ti is substituted for external-surface B in UCB-4 catalyst (denoted as Ti-UCB-4). Ti-UCB-4 is synthesized by (i) delaminating boron-containing B-SSZ-70; (ii) synthesizing silanol nests in locations previously occupied by boron, followed by (iii) reoccupying some of these silanol nests located on the external surface of the delaminated zeolite with grafted Ti heteroatoms via condensation of a Ti precursor molecule to the silanol nests. Comparison of Ti-UCB-4 with the conventional catalyst consisting of isolated grafted Ti sites on the surface of amorphous silica demonstrates at least an equal amount of accessibility to bulky reactants such as oxidant reagent tert-butyl-hydroperoxide (TBHP). This accessibility is enabled by framework Ti sites being located near the external surface in Ti-UCB-4. Yet Ti-UCB-4 exhibits improved performance in the form of a higher olefin-epoxidation catalytic activity, robustness, and selectivity when using organic hydroperoxide as oxidant, compared to the conventional catalyst consisting of grafted Ti sites on the surface of amorphous silica. This improved performance is specifically due to the Ti sites being located within a zeolitic rather than amorphous silica framework in Ti-UCB-4. This role of the framework is further demonstrated by comparing delaminated zeolites Ti-DZ-1 with Ti-UCB-4, in which Ti sites are both located within a zeolitic framework, albeit different between the former and latter. The latter (Ti-UCB-4) catalyst exhibits a significantly higher activity for olefin epoxidation using organic hydroperoxide as oxidant compared to the former on a per Ti basis. However, when comparing Sn-DZ-1 with Sn-UCB-4, it is the former (Sn-DZ-1) that exhibits a significantly higher activity for Baeyer-Villiger oxidation with hydrogen peroxide. Therefore, the choice of optimal zeolite framework is highly nonobvious and can be both dependent on the reaction (olefin epoxidation versus Baeyer-Villiger oxidation) and metal heteroatom (i.e. Sn versus Ti) composition.

The process of the present invention, therefore, is a process of conducting olefin epoxidation which comprises contacting an olefin and an oxidant in the presence of a Ti-UCB-4 catalyst to thereby prepare an oxide. The olefin can be any suitable olefin, but in one embodiment has from 3-12 or more carbon atoms. Examples of suitable olefins include propylene and octene. Alternatively, the olefin can comprise more than 12 carbon atoms, and such olefins are typically expodized in the fine chemicals and pharmaceuticals area since epoxides are known to be key intermediates for synthesis of complex molecules. The oxidant can be any suitable oxidant, but TBHP is preferred. As a solvent, any suitable hydrocarbon solvent can be used, for example any solvent comprising an alkane, such as octane.

The most preferred catalyst is prepared by delaminating a B-SSZ-70 precursor zeolite material and substituting Ti atoms for the boron atoms on the external surface of the zeolite material lattice framework. The Ti-UCB-4 catalyst is prepared using this process.

The following examples are provided to further illustrate the present invention, but are not meant to be limiting.

Details of Synthesis and Characterization of Materials Prepared for Use in the Examples Synthesis of ERB-1 Precursor (ERB-1P).

The synthesis of this material followed previously known and described procedures. In this procedure, 2.40 g of NaOH (EMD Chemicals, 97%) and 6.18 g of $H_3BO_3$ (≥99.5%, Fisher Chemical) were dissolved in 30 mL of nanopure $H_2O$, and 12.8 g of PI (≥99.5%, purified by redistillation, Sigma-Aldrich). To this mixture, 9.0 g of $SiO_2$ (Aerosil® 200, Evonik-Degussa) and 0.10 g of seed crystals (as-made ERB-1P, Si/B=11) were added. A white viscous gel was obtained after mixing with a spatula. The gel composition in molar ratios was $SiO_2$:0.33 $B_2O_3$:0.2 $Na_2O$:1.0 PI:11.0 $H_2O$. This gel was subsequently transferred to a 125 mL Parr reactor equipped with a Teflon liner. The reactor was heated at 175° C. for a period of 7-9 days without agitation. After cooling, the contents were poured into a filter, and the precipitated solids were washed several times with deionized water and then air dried. The characterization of material ERB-1 after calcination (denoted ERB-1C) is given in Table 1 and matches previous specifications for this material.

Synthesis of DZ-1.

The synthesis of this material followed previously known and described procedures. In this procedure, 1.0 g of zeolite precursor and either 4.0 g of $Zn(NO_3)_2.6H_2O$ or $Mn(NO_3)_2.4H_2O$ were added to 35 g of pH 1 $HNO_3$ solution in a 125 mL sealed thick-walled glass reactor, under vigorous stirring. The mixture was heated at 135° C. for 16 h. The resulting delaminated material was denoted as DZ-1. The solid product was collected on a filter, washed thoroughly with water, and finally air-dried. The characterization of material DZ-1 is given in Table 1 and matches previous specifications for this material.

Synthesis of Ti-DZ-1.

The synthesis of this material was described previously and is also described herein for completion. In this procedure, 4 g $Ti(OC_4H_9)_4$ was added to 1 g of DZ-1 to make a viscous slurry in a sealed, thick-walled glass reactor at 150° C. The slurry was vigorously stirred for 1 h. Then the temperature of 120° C. was lowered and 20 mL of n-BuOH was added into the slurry. The resulting slurry was stirred for an additional 10 min. The solid product was collected on a filter, washed thoroughly with n-BuOH to remove residual $Ti(OC_4H_9)_4$ and surface-grafted Ti species, followed by acetone to remove residual n-BuOH, and finally was air-dried. The resulting material is denoted as Ti-DZ-1, and its full characterization has been previously described. The characterization of material Ti-DZ-1 is given in Table 1 and matches previous specifications for this material.

Synthesis of B-SSZ-70 Precursor.

B-SSZ-70 precursor was synthesized using the same method as described previously in I. Ogino, E. A. Eilertsen, S.-J. Hwang, T. Rea, D. Xie, X. Ouyang, S. I. Zones, A. Katz, Chem. Mater., 2013, 25, 1502-1509. Gel compositions were $SiO_2$:0.033 $B_2O_3$:0.050 $Na_2O$:0.20 SDA (1,3-bis (isobutyl)imidazolium): 30 $H_2O$. The gel was sealed in a 23-mL Parr reactor and heated while tumbling the reactor at 60 rpm at 150° C. for a period of 1-2 weeks. After cooling, the contents were poured into a filter, and the precipitated solids were washed several times with water and then air dried.

Synthesis of UCB-4.

UCB-4 was synthesized based on previous literature. In this procedure, a mixture of 0.50 g of B-SSZ-70 precursor, 0.55 g of cetyltrimethylammonium bromide (CTAB), 0.85 g of tetrabutylammonium fluoride trihydrate (TBAF), and 0.85 g of tetrabutylammonium chloride (TBACl) in 20 mL of DMF was placed in a sealed, thick-walled glass reactor, and stirred at 100° C. for 72 h in an oil bath. After cooling, the slurry was sonicated for 1 h in an ice bath, using a Branson digital sonifier 450 (Branson, USA) operating under pulse mode (1.0 s on and 0.1 s off). The sonicated slurry was filtered, to separate a solid from a brown-colored filtrate. The solid was washed with DMF and then with ethanol, thoroughly, and dried at 60° C. overnight, yielding a white solid, followed by calcination in air at 550° C. (ramp rate 1° C./min from r.t.) for 5 h. The characterization of material UCB-4 is given in Table 1 and matches previous specifications for this material.

Synthesis of Deboronated UCB-4.

20 mL of 2.0 N HNO₃ solution was added to 0.50 g of the as-made UCB-4 in a sealed, thick-walled glass reactor, and stirred at 100° C. for 24 h. The solid product was collected on a filter, washed thoroughly with deionized water, and was then air-dried.

Synthesis of Ti-UCB-4.

4 g Ti(OC₄H₉)₄ was added to 1 g of deboronated UCB-4 to make a viscous slurry in a sealed, thick-walled glass reactor at 150° C. The slurry was vigorously stirred for 1 h. The temperature was subsequently lowered to 120° C., and 20 mL of n-BuOH was added into the slurry. The resulting slurry was stirred for 10 min. The solid product was collected on a filter, washed thoroughly with n-BuOH to remove residual Ti(OC₄H₉)₄ and surface-grafted Ti species, followed by acetone to remove residual n-BuOH, and was finally air-dried. The resulting material is denoted as Ti-UCB-4. The characterization of material Ti-UCB-4 is given in Table 1 and matches previous specifications for this material.

Acid Treatment of Ti-UCB-4.

Figure 1B:
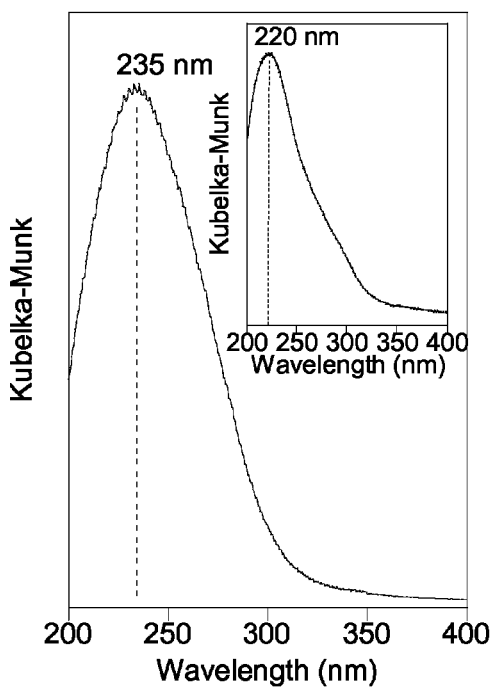

50 mL of 2 N HNO₃ was added to 100 mg of Ti-UCB-4 in a sealed, thick-walled glass reactor at 100° C. The mixture was vigorously stirred for 1 h before being cooled down to room temperature. The solid was collected on a filter, washed thoroughly with deionized water followed by acetone, and was finally air-dried. Data in FIGS. 1A and 1B demonstrate that both zeolite samples consisting of Ti-DZ-1 and Ti-UCB-4 consist of Ti within non-octahedral coordination environments, since a band would otherwise appear around 330 nm for octahedral Ti species as in anatase. Other data in Table 1 show the increase in surface area for delaminated zeolite materials DZ-1 and Ti-DZ-1 relative to three-dimensional calcined zeolite ERB-1C. In the discussion herein, Ti/SiO₂ refers to isolated Ti-on-silica sites that are similar in all respects to the conventional Ti-on-amorphous-silica sites previously described in the literature. In the examples here, Ti/SiO₂ catalyst was synthesized by combusting a titanocalixarene site on silica to synthesize isolated Ti sites on amorphous silica as described previously (see Notestein, J. M.; Andrini, L. R.; Kalchenko, V. I.; Requejo, F. G; Katz, A.; and Iglesia, E.; Journal of the American Chemical Society 2007, 129, 1122-1131).

TABLE 1

Synthesis Conditions and Physicochemical Properties of DZ-1 Related Materials

| Sample[a] | Heteroatom (M) | Metal precursor | Si/Ti Ratio | Si/B ratio | $V_{micro}$[c] (cm³/g) | $V_{meso}$[d] (cm³/g) | $S_{ext}$[e] (m²/g) |
|---|---|---|---|---|---|---|---|
| ERB-1C | B | n/a | n/a | 10 | 0.12 | 0.04 | 53 |
| UCB-4 | B | n/a | n/a | 30 | 0.12 | 0.08 | 96 |
| DZ-1 | n/a | n/a | n/a[b] | >200 | 0.08 | 0.10 | 131 |
| Ti-DZ-1 | Ti | Ti(OC₄H₉)₄ | 67 | >200 | 0.04 | 0.14 | 171 |
| Ti-UCB-4 | Ti | Ti(OC₄H₉)₄ | 88 | >200 | 0.14 | 0.08 | 90 |

[a] All the samples in Table 1 are calcined materials;
[b] The Si/Zn ratio for DZ-1 is >200;
[c] Micropore volume determined by t-plot method;
[d] Mesopore (between 1 and 10 nm in diameter) volume determined by NLDFT method;
[e] External surface area determined by t-plot method.

While the examples above substitute Ti into the silanol nest created by removing framework boron, it should be mentioned that the substitution of other metals of catalytic relevance and specifically Lewis-acid-catalytic relevance can be achieved using the methods described, for example, in U.S. Ser. No. 14/291,489, noted above, and expressly incorporated by reference herein above.

Epoxidation-Catalysis Example 1

Figure 2A:
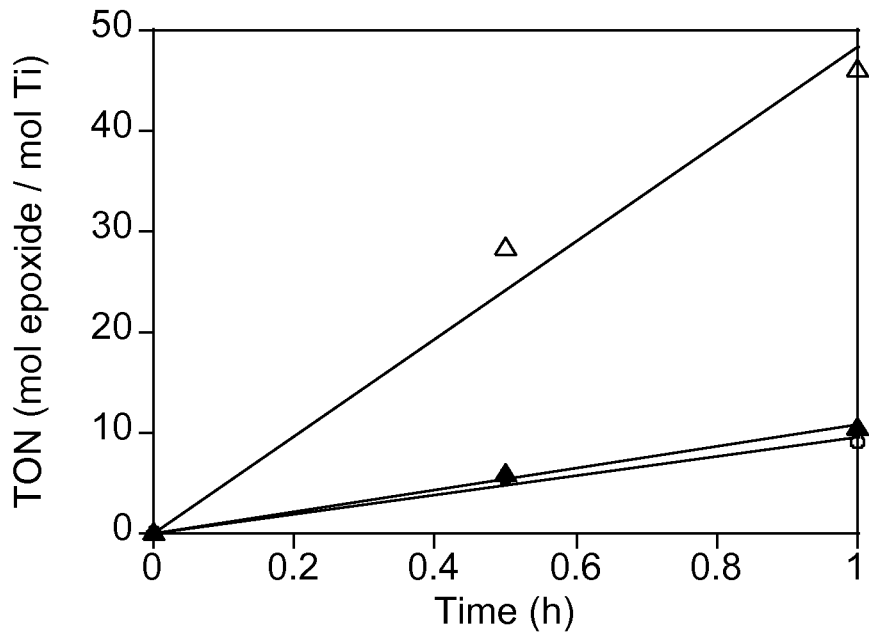
FIG. 2A shows catalytic kinetics of time versus TON normalized by mmol Ti sites and FIG. 2B shows epoxide yield versus epoxide selectivity of 1-octene reacting with TBHP over Ti-UCB-4 (Δ), Ti-DZ-1 (▲), Ti/SiO$_2$ (○) materials.
Figure 2B:
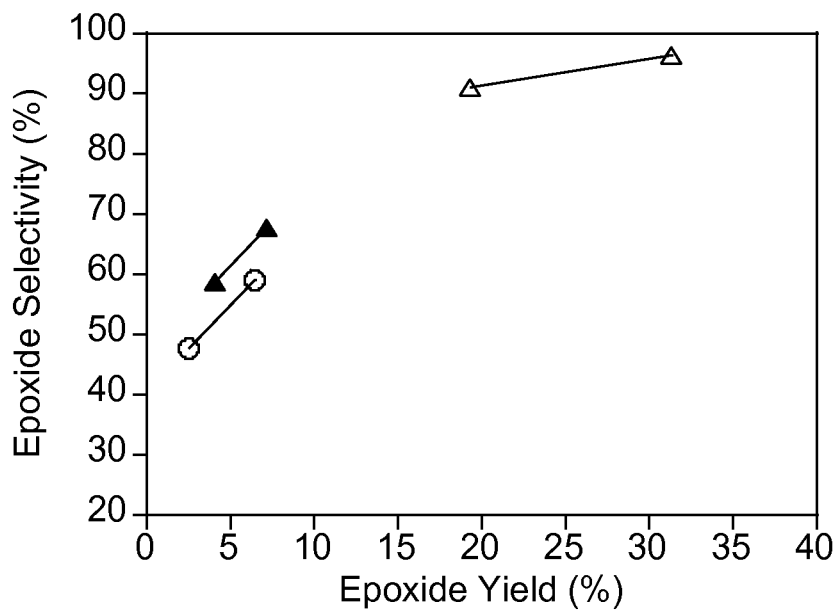

To perform catalysis, 25 mg of catalyst, 5.9 mmol of 1-octene, and 20 mL of octane as solvent was combined to make a slurry at 60° C., to which 0.59 mmol of TBHP was added. The catalysis results are shown in FIGS. 2A and 2B, and are summarized in Table 2 below. The Ti-UCB-4 catalyst has an initial rate of epoxidation catalysis (normalized per Ti atom) that is 5-fold faster than both Ti-DZ-1 and Ti/SiO₂ catalysts. Even at a low TBHP conversions of 20%-30%, the selectivity (defined as epoxide formed divided by TBHP consumed) for Ti-UCB-4 is above 90%, which is much higher than typical selectivities for the Ti/SiO₂ catalyst. This initial-rate comparison also holds when considering the number of turnovers (TON) at 2 h of reaction time. This TON is 3.6-fold and 4.5-fold higher for Ti-UCB-4 relative to Ti-DZ-1 and Ti/SiO2, respectively.

Epoxidation-Catalysis Example 2

Figure 3A:
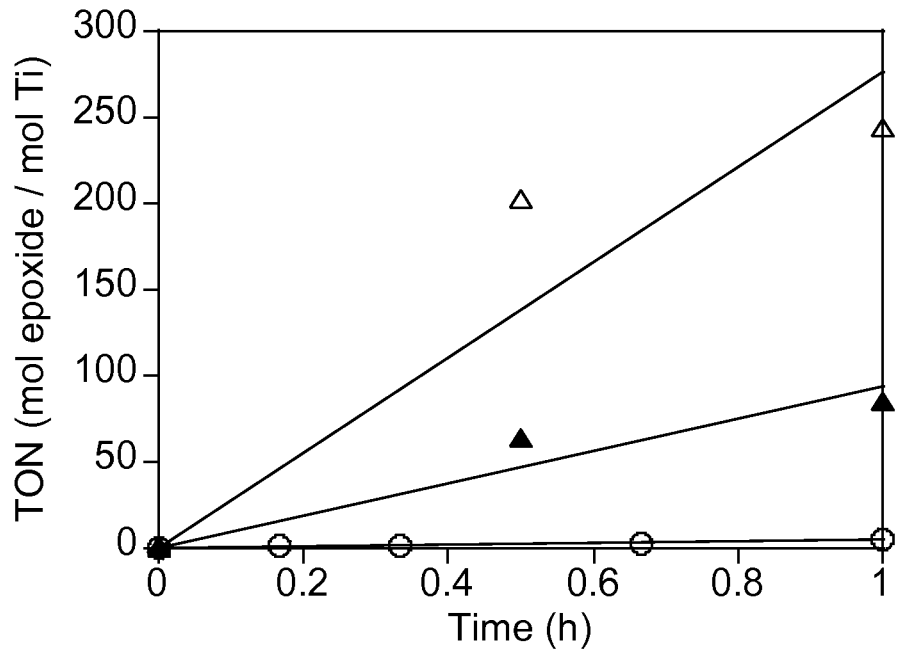
FIG. 3A shows catalytic kinetics of time versus TON normalized by mmol Ti sites and FIG. 3B shows epoxide yield versus epoxide selectivity of 1-octene reacting with TBHP over Ti-UCB-4 (Δ) Ti-DZ-1 (▲), and Ti/SiO$_2$ (○) materials.
Figure 3B:
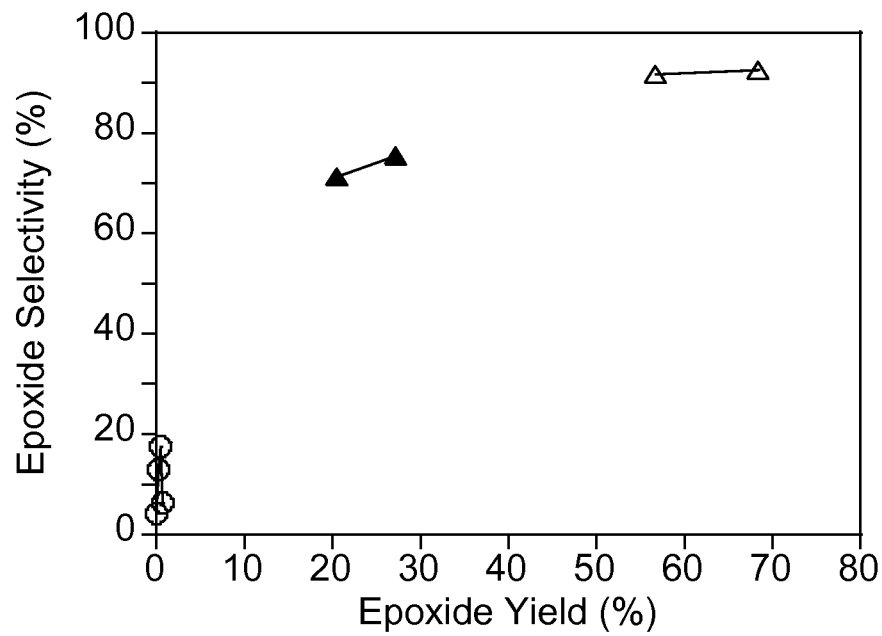

To perform catalysis, 25 mg of catalyst, 3.0 mmol of 1-octene, and 10 mL of octane as solvent was combined so as to make a slurry at 110° C., to which 1.5 mmol of TBHP was added. Results are represented in FIGS. 3A and 3B and Table 2. Under these conditions of high temperature and high TBHP concentration, Ti-UCB-4 is both the most active as well as selective of catalysts, having an initial rate per Ti site that is 3.2-fold higher than DZ-1. This again demonstrates how the choice of zeolite framework (MWW-type of framework in DZ-1 versus SSZ-70 in UCB-4) controls the Ti catalyst epoxidation activity and selectivity. At these extremely harsh conditions, Ti/SiO₂ shows poor activity and selectivity relative to both zeolite catalysts Ti-DZ-1 and Ti-UCB-4. This reinforces the benefit of having Ti within a zeolitic rather than amorphous framework, and this benefit is further made clear by a comparison of the initial rate differences per Ti site for the zeolitic and amorphous silica Ti catalysts, which differ by more than 17 fold.

Epoxidation-Catalysis Example 3

Figure 4A:
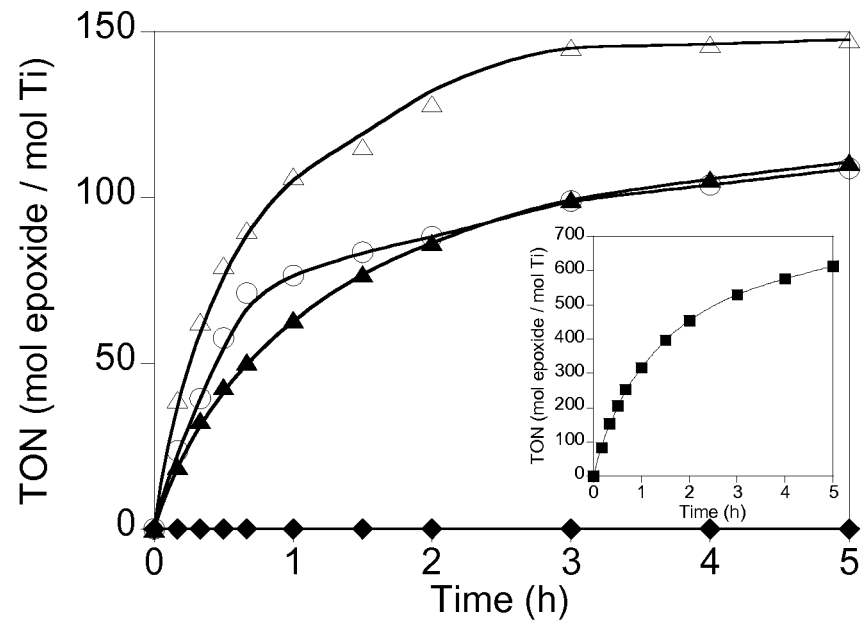
FIG. 4A shows catalytic kinetics of time versus TON normalized by mmol Ti sites and FIG. 4B shows epoxide yield versus epoxide selectivity of cyclohexene reacting with TBHP over Ti-UCB-4 (Δ), Ti-DZ-1 (▲), and Ti/SiO$_2$ (○) materials. (Reaction condition: 25 mg of catalyst, 0.59 mmol of TBHP, 5.9 mmol of cyclohexene, 20 mL of octane as solvent, 60° C.)
Figure 4B:
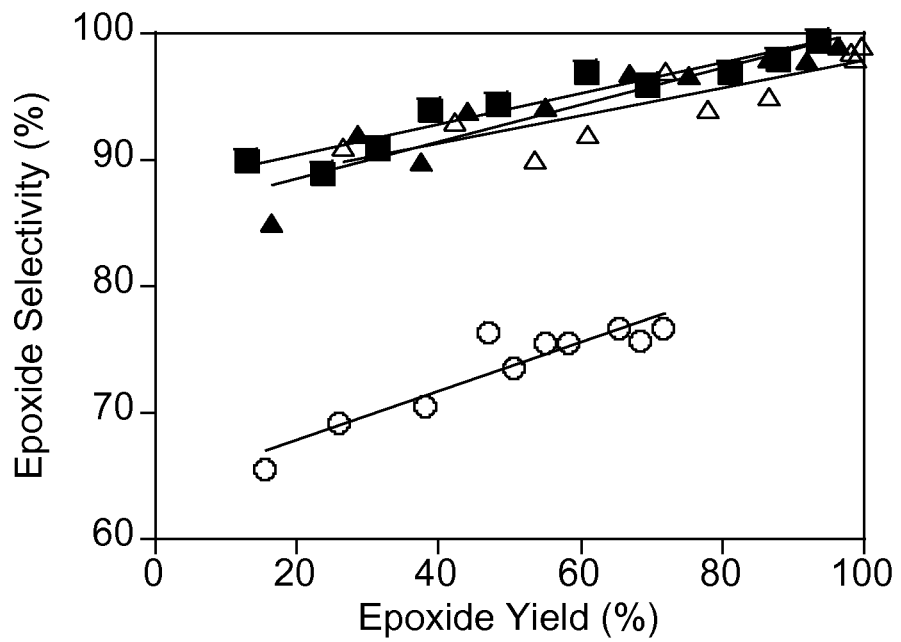

To perform catalysis, 25 mg of catalyst, 5.9 mmol of cyclohexene, and 10 mL of octane as solvent were combined to make a slurry at 110° C., to which 0.59 mmol of TBHP was added. Results are represented in FIGS. 4A and 4B and Table 2. From the kinetics data, it is evident that the epoxidation kinetics are not first order for both zeolite catalysts, with rates not deviating significantly from the initial rate even at a conversion of ~70% for both Ti-UCB-4 and Ti-DZ-1. On the other hand, above 50% conversion for Ti/SiO$_2$, there is severe deactivation under the same conditions. Both Ti zeolite catalysts also show much higher epoxide selectivity than Ti/SiO$_2$. Thus both the activity and selectivity of the Ti-zeolite catalysts is superior to the amorphous-silica catalyst. The inset of FIG. 4b shows results on the acid-washed Ti-UCB-4, which has the highest rate per Ti site of all catalysts and therefore shows the benefit of the acid wash on increasing this rate.

Epoxidation-Catalysis Example 4

Figure 5A:
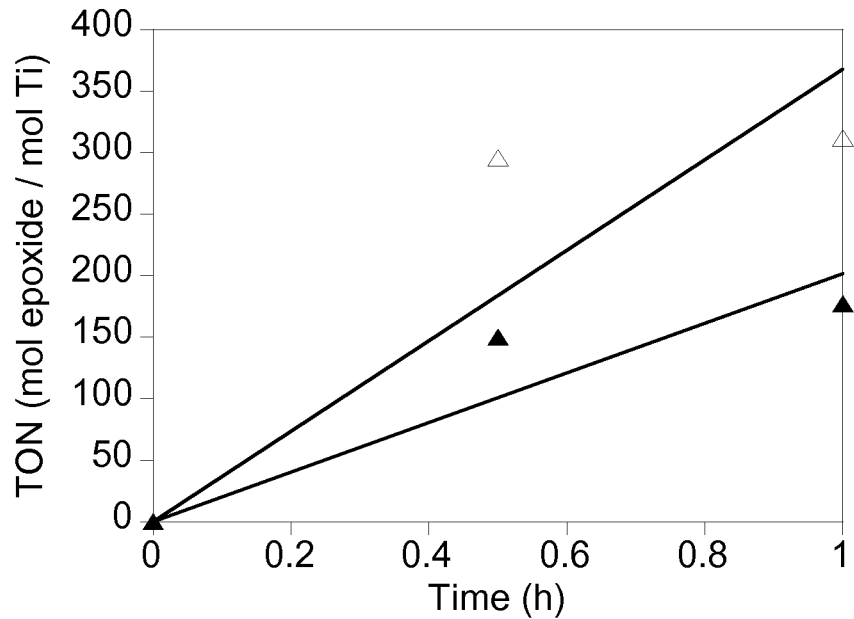
FIG. 5A shows catalytic kinetics of time versus TON normalized by mmol Ti sites and FIG. 5B epoxide yield versus epoxide selectivity of 1-octene reacting with TBHP over Ti-UCB-4 (Δ) and Ti-DZ-1 (▲).
Figure 5B:
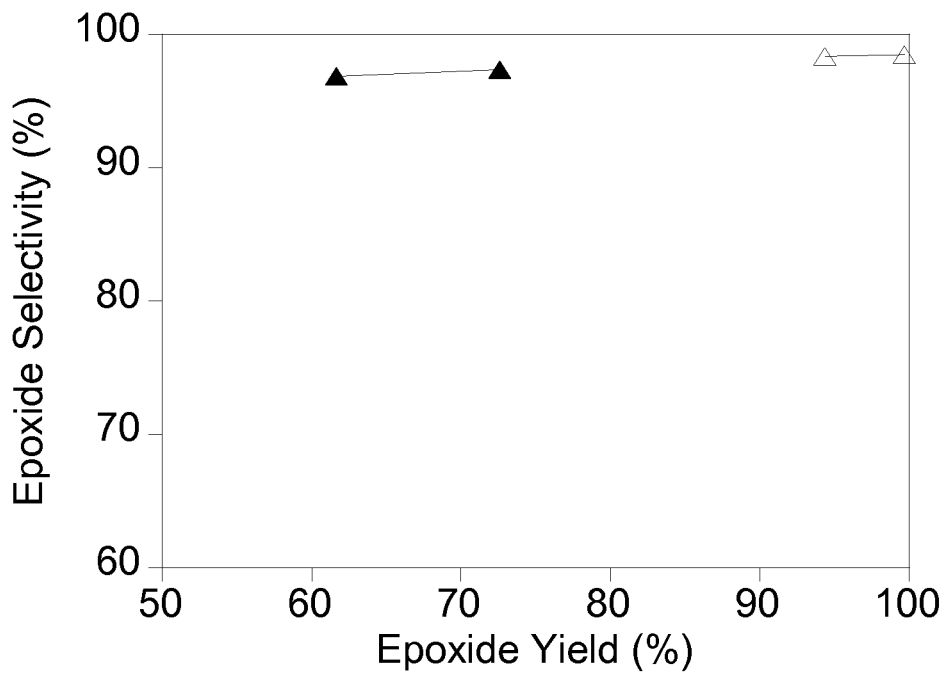

To perform catalysis, 20 mg of catalyst and 0.315 g of cyclohexene were combined to make a slurry at 60° C., to which 0.2 mL of 5.0 M TBHP in nonane was added. Results are represented in FIGS. 5A and 5B and Table 2. Under these conditions of solvent-free and high TBHP concentration, Ti-UCB-4 is more active and selective than Ti-DZ-1, having an initial rate per Ti site of 5210 mol mol$_{Ti}^{-1}$ min$^{-1}$ that is 1.8-fold higher than DZ-1. This again demonstrates how the choice of zeolite framework (MWW-type of framework in DZ-1 versus SSZ-70 in UCB-4) controls the Ti catalyst epoxidation activity and selectivity. Compared to another type of supported Ti delaminated zeolite catalysts, Ti/ITQ-2, which typically have an initial rate per Ti site of ~40 mol mol$_{Ti}^{-1}$ min$^{-1}$, the rate exhibited by Ti-UCB-4 in FIGS. 5A and 5B is about 130-fold faster than Ti/ITQ-2, under similar solvent-free conditions.

Epoxidation—Catalysis Summary

Even under mild conditions with an easy-to-epoxidize reactant such as cyclohexene (conditions C and D), Ti-UCB-4 is significantly more active than Ti-DZ-1. However, these differences are further accentuated in favor of Ti-UCB-4 when using a more difficult-to-epoxidize reactant, a terminal rather than internal alkene, such as 1-octene (conditions A and B), where Ti-UCB-4 is up to 5-fold more active in terms of k compared with Ti-DZ-1. Such a terminal alkene is more relevant because it is a better model of propylene—an olefin used for epoxidation on an industrial scale. All of these comparisons demonstrate the importance of the zeolite framework in controlling the catalytic activity at the heteroatom center—wherein the heteroatom serves as a center for Lewis-acid catalysis (epoxidation in the examples above). Such a conclusion is further reinforced when considering the performance of the conventional catalyst consisting of isolated grafted Ti sites on amorphous silica (Ti/SiO$_2$) as a control, which for 1-octene at high temperature (condition B) is 55-fold less active compared with Ti-UCB-4 in terms of k. Both zeolite-based catalysts are more robust and deactivate less compared with the conventional Ti/SiO$_2$ catalyst, as shown by data using condition C in FIGS. 4A and 4B. These data reinforce the advantages of using catalysts of the present invention as olefin epoxidation catalysts when using an organic hydroperoxide as oxidant.

What is claimed is:

1. A process of conducting olefin epoxidation which comprises contacting an olefin and an oxidant in the presence of a Ti-UCB-4 to thereby prepare an epoxide.

2. The process of claim 1, wherein the olefin has from 3-12 carbon atoms.

3. The process of claim 2, wherein the olefin is propylene.

4. The process of claim 1, wherein the olefin has greater than 12 carbon atoms.

5. The process of claim 1, wherein the oxidant is tert-butyl hydroperoxide or cumene hydroperoxide.

6. The process of claim 1, wherein a solvent is used for the reaction which comprises an alkane.

TABLE 2

Epoxidation of olefins with TBHP Catalyzed by Various Zeolite Catalysts

| Sample | Ti (wt %) | Reactant | Reaction condition [a] (T° C.) | k [b] (mol mol$_{Ti}^{-1}$min$^{-1}$) | TON [c] | Epoxide yield (%) [d] | Epoxide Selectivity (%) |
|---|---|---|---|---|---|---|---|
| Ti-DZ-1 | 0.98 | 1-octene | A (60° C.) | 50 | 20 | 24 | 70 |
|  |  | 1-octene | B (110° C.) | 583 | 100 | 36 | 63 |
|  |  | Cyclohexene | C (60° C.) | 533 | 86 | 99 | >99 |
|  |  | Cyclohexene | D (60° C.) | 2951 | 177 | 73 | 97 |
| Ti-UCB-4 | 0.76 | 1-octene | A (60° C.) | 250 | 72 | 72 | 97 |
|  |  | 1-octene | B (110° C.) | 1867 | 262 | 76 | 84 |
|  |  | Cyclohexene | C (60° C.) | 1333 | 128 | 99 | >99 |
|  |  | Cyclohexene | D (60° C.) | 5210 | 312 | 99 | 99 |
| Ti/SiO$_2$ | 0.77 | 1-octene | A (60° C.) | 50 | 16 | 22 | 77 |
|  |  | 1-octene | B (110° C.) | 33 | 9 | 3 | 26 |
|  |  | Cyclohexene | C (60° C.) | 650 | 88 | 72 | 76 |
| Acid washed Ti-UCB-4 | 0.24 | Cyclohexene | C (60° C.) | 4500 | 455 | 99 | >99 |
| TS-1 | 0.85 | Cyclohexene | C (60° C.) | 0 | 0 | 0 | n/a |

[a] Reaction condition: (A) 25 mg of zeolite catalyst, 0.59 mmol of TBHP, 5.9 mmol of 1-octene, 20 mL of octane as solvent, 60° C.; (B) 25 mg of catalyst, 1.5 mmol of TBHP, 3.0 mmol of 1-octene, 10 mL of octane as solvent, 110° C.; (C) 25 mg of zeolite catalyst, 0.59 mmol of TBHP, 5.9 mmol of cyclohexene, 20 mL of octane as solvent, 60° C.; (D) 20 mg of catalyst, 1.0 mmol of TBHP, 3.8 mmol of cyclohexene, 60° C.
[b] k is calculated when the epoxide yield is under 20%;
[c] TON values are calculated by dividing the moles of epoxide formed at 2 h by the moles of Ti sites;
[d] Epoxide yields are calculated by dividing the moles of epoxide formed at 5 h by the moles of TBHP at 0 h.

7. The process of claim 1, wherein a solvent is used for the reaction which comprises octane.

8. The process of claim 1, wherein the Ti-UCB-4 catalyst is prepared by delaminating a B-SSZ-70 precursor and substituting Ti atoms for the boron atoms on the surface of the zeolite material lattice framework.

9. The process of claim 1, wherein the Ti-UCB-4 comprises a zeolite material having Ti heteroatoms on the external surface of the zeolite material lattice framework, and B heteroatoms, or silanols created from boron hydrolysis, throughout the remainder of the lattice framework.

10. The process of claim 9, wherein the lattice framework of the Ti-UCB-4 comprises large pore 12 member ring or larger openings at the external surface of the framework, and 10 member ring or smaller openings beneath the external surface large pore openings.

11. The process of claim 10, wherein the external surface of the framework comprises 12 member ring openings with 10 member ring openings beneath the external surface 12 member ring openings.

12. A process of conducting olefin epoxidation which comprises contacting an olefin and an oxidant in the presence of a catalyst to thereby prepare an epoxide, where the catalyst is prepared by delaminating a B-SSZ-70 precursor and substituting Ti atoms for the boron atoms on the external surface of the zeolite material lattice framework.

13. The process of claim 12, wherein the olefin has from 3-12 carbon atoms.

14. The process of claim 13, wherein the olefin is propylene.

15. The process of claim 12, wherein the olefin has greater than 12 carbon atoms.

16. The process of claim 12, wherein the oxidant is tert-butyl hydroperoxide or cumene hydroperoxide.

17. The process of claim 12, wherein a solvent is used for the reaction which comprises an alkane.

18. The process of claim 12, wherein a solvent is used for the reaction which comprises octane.

* * * * *